(12) United States Patent
Nelson et al.

(10) Patent No.: US 7,913,693 B2
(45) Date of Patent: Mar. 29, 2011

(54) METHOD AND APPARATUS FOR PREVENTING OCCLUSION OF A TRACHEAL TUBE SUCTION LUMEN

(75) Inventors: Donald S. Nelson, San Ramon, CA (US); Roger S Mecca, Danville, CA (US); David B. Swedlow, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1141 days.

(21) Appl. No.: 11/595,223

(22) Filed: Nov. 10, 2006

(65) Prior Publication Data

US 2008/0110468 A1  May 15, 2008

(51) Int. Cl.
*A61M 16/00* (2006.01)
*A61M 25/00* (2006.01)

(52) U.S. Cl. .............. 128/207.14; 128/207.15; 604/266; 604/268

(58) Field of Classification Search ............. 128/200.24, 128/200.26, 205.19, 207.14–207.29; 604/30, 604/33, 35, 39, 41, 96.01, 118, 119, 121, 604/128, 129, 256, 266, 268, 533, 534, 537, 604/539, 284

See application file for complete search history.

(56) References Cited

U.S. PATENT DOCUMENTS

| | | | |
|---|---|---|---|
| 3,625,793 A | 12/1971 | Sheridan | |
| 3,884,242 A | 5/1975 | Bazell et al. | |
| 3,948,273 A | 4/1976 | Sanders | |
| 4,214,593 A | 7/1980 | Imbruce et al. | |
| 4,305,392 A | 12/1981 | Chester | |
| 4,344,436 A | 8/1982 | Kubota | |
| 4,423,725 A | 1/1984 | Baran et al. | |
| 4,488,548 A | 12/1984 | Agdanowski | |
| 4,498,473 A | 2/1985 | Gereg | |
| 4,502,482 A | 3/1985 | DeLuccia et al. | |
| 4,607,635 A | 8/1986 | Heyden | |
| 4,751,924 A | 6/1988 | Hammerschmidt et al. | |
| 4,840,173 A | 6/1989 | Porter, III | |
| 5,040,531 A | 8/1991 | Coleman et al. | |
| 5,058,577 A | 10/1991 | Six | |
| 5,067,497 A | 11/1991 | Greear et al. | |
| 5,201,310 A | 4/1993 | Turnbull | |
| 5,431,637 A | 7/1995 | Okada et al. | |
| 5,445,144 A | 8/1995 | Wodicka et al. | |
| 5,501,215 A | 3/1996 | Huerta | |

(Continued)

FOREIGN PATENT DOCUMENTS

EP 0665029 8/1995

(Continued)

OTHER PUBLICATIONS

International Search Report PCT/US2007/023713, 7 pages, mailed Feb. 3, 2009.

(Continued)

*Primary Examiner* — Justine R Yu
*Assistant Examiner* — Rachel T Young
(74) *Attorney, Agent, or Firm* — Fletcher Yoder (57) ABSTRACT

There is provided a medical tube lumen plug, including: a plug, including: a body configured to be mechanically coupled to a lumen of a medical tube; and a protrusion configured to extend external to the medical tube, wherein the protrusion is configured to prevent occlusion of an aperture, wherein the aperture is configured to provide a pathway between the lumen and a region external to the medical tube.

35 Claims, 7 Drawing Sheets

U.S. PATENT DOCUMENTS

| | | | |
|---|---|---|---|
| 5,582,167 A | 12/1996 | Joseph | |
| 5,676,635 A | 10/1997 | Levin | |
| 5,730,727 A * | 3/1998 | Russo | 604/118 |
| 5,819,723 A | 10/1998 | Joseph | |
| 5,890,516 A * | 4/1999 | Talamonti | 137/605 |
| 5,899,884 A * | 5/1999 | Cover et al. | 604/119 |
| 6,062,223 A | 5/2000 | Palazzo et al. | |
| 6,550,475 B1 | 4/2003 | Oldfield | |
| 6,849,042 B2 | 2/2005 | Christopher | |
| 7,052,456 B2 | 5/2006 | Simon | |
| 7,089,942 B1 | 8/2006 | Grey | |
| 7,152,603 B1 | 12/2006 | Crump et al. | |
| 7,156,827 B2 | 1/2007 | McNary et al. | |
| 7,191,782 B2 | 3/2007 | Madsen | |
| 7,258,120 B2 | 8/2007 | Melker | |
| 7,273,050 B2 | 9/2007 | Wei | |
| 7,293,561 B2 * | 11/2007 | Madsen et al. | 128/207.14 |
| 7,300,415 B2 | 11/2007 | McMurtry et al. | |
| 7,419,479 B2 * | 9/2008 | Quinn | 604/270 |
| 7,478,636 B2 | 1/2009 | Madsen et al. | |
| 7,503,328 B2 | 3/2009 | Kolobow et al. | |
| 2001/0005788 A1 | 6/2001 | McGuchkin, Jr. | |
| 2001/0012927 A1 | 8/2001 | Mauch | |
| 2001/0054425 A1 | 12/2001 | Bertram | |
| 2002/0014238 A1 | 2/2002 | Kotmel | |
| 2003/0040703 A1 | 2/2003 | Rauker et al. | |
| 2003/0216688 A1 | 11/2003 | M.A.J.M. et al. | |
| 2003/0216690 A1 * | 11/2003 | Foley | 604/119 |
| 2003/0233068 A1 | 12/2003 | Jayaraman | |
| 2004/0221853 A1 | 11/2004 | Miller | |
| 2005/0039754 A1 | 2/2005 | Simon | |
| 2006/0138379 A1 * | 6/2006 | Jacobsen et al. | 251/344 |
| 2007/0028924 A1 | 2/2007 | Madsen et al. | |
| 2007/0028925 A1 | 2/2007 | Madsen et al. | |
| 2007/0044806 A1 | 3/2007 | Madsen et al. | |
| 2007/0044807 A1 | 3/2007 | Madsen et al. | |
| 2007/0089748 A1 * | 4/2007 | Madsen et al. | 128/207.15 |
| 2007/0270766 A1 * | 11/2007 | Kucklick | 604/256 |
| 2008/0011304 A1 | 1/2008 | Stewart | |
| 2008/0047562 A1 * | 2/2008 | Colburn et al. | 128/207.14 |
| 2008/0099025 A1 | 5/2008 | MacMillan | |
| 2008/0110468 A1 | 5/2008 | Nelson et al. | |
| 2008/0210235 A1 | 9/2008 | Field et al. | |
| 2008/0257353 A1 | 10/2008 | Yamamoto et al. | |
| 2009/0038620 A1 | 2/2009 | Efrati | |

FOREIGN PATENT DOCUMENTS

| | | |
|---|---|---|
| WO | WO 2005/112796 A | 12/2005 |
| WO | WO 2005112796 | 12/2005 |
| WO | WO2005118039 | 12/2005 |

OTHER PUBLICATIONS

Kolobow, Theodor; "The Mucus Slurper: a novel tracheal tube that requires no tracheal tube suctioning. A preliminary report;" Intensive Care Medical, 2006, 32:1414-1418.

Clinical Trials; "Coated Endotracheal Tube and Mucus Shaver to Prevent Hospital-Acquired Infections," National Institutes of Health Clinical Center, 2007, NCT00341354, 3 pages.

Clinical Trials, "Prevent of Pneumonia Comparing Ceftriaxone With Subglottic Aspiration," Hospital Universitario Principe de Asturias, Sep. 2006; NCT00374959.

* cited by examiner

METHOD AND APPARATUS FOR PREVENTING OCCLUSION OF A TRACHEAL TUBE SUCTION LUMEN

BACKGROUND OF THE INVENTION

1. Field of the Invention

The present invention relates to medical devices and, more particularly, to airway products, such as tracheal tubes and medical devices inserted into the trachea of a patient to facilitate mechanical ventilation of a patient's lungs.

2. Description of the Related Art

This section is intended to introduce the reader to various aspects of art that may be related to aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

During the course of medical care, a tube or other medical device may be used to control the flow of air, fluids and foods into a patient. For example, medical devices, such as tracheal tubes, are often inserted into the trachea of a patient to provide a pathway for transferring air, oxygen, drugs, or anesthetic gases into the lungs. Other devices may be inserted into the body to transfer liquid, food or other substances into and out of a patient. While the tube is inserted into the patient, a seal may be formed between the tube and the tracheal wall to control the flow of substances. For example, an inflatable cuff may surround a portion of the tracheal tube, and the cuff may be inflated after the tracheal tube has been inserted into the trachea of a patient. Once inflated, the cuff may provide a seal between the tracheal tube and the tracheal wall. The seal may prevent secretions above the tracheal tube from leaking past the tube and into the lungs of the patient, as well as, prevent air that is introduced into the lungs through the tracheal tube from escaping via the trachea. In this configuration, the flow of substances through the trachea may be limited to the flow in the tube or other medical device. This may allow a medical practitioner to maintain control over the type and amount of substances flowing into and out of the patient's trachea.

Although these techniques are beneficial, some challenges remain. For example, secretions tend to flow down the trachea and settle just above the seal location. To remove and limit the build up of these secretions, various methods have been developed. For example, some tracheal tubes may include a fluid removal lumen that runs the length of the tube and that terminates at an aperture located just above the inflatable cuff. In such a configuration, the fluid build up may be periodically or continuously evacuated via a vacuum attached to the fluid removal lumen, where the vacuum provides suction at the aperture of the tracheal tube. Although the evacuation process may provide for removal of secretions, it may be possible for the aperture to be come occluded. For example, during evacuation, the aperture may come in contact with the wall of the trachea. When this happens, the suction may pull the tracheal wall against the aperture, occluding the aperture and preventing removal of the secretions.

Accordingly, it is desirable that a medical device, such as a tracheal tube, include a component that is designed to prevent occlusion of the evacuation pathway.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one exemplary embodiment, a medical tube lumen plug, comprising: a plug comprising: a body configured to be mechanically coupled to a lumen of a medical tube proximate an aperture in the tube; and a protrusion configured to extend external to the medical tube to prevent occlusion of the aperture, wherein the aperture is configured to provide a pathway between the lumen and a region external to the medical tube.

There is also provided a medical tube comprising: an elongated tube comprising: a tubular body: a lumen that extends along the tubular body to provide a passageway for the removal of fluids and gases; a sealing member on the tubular body that is configured to provide a seal between the tubular body and a body cavity wall; and an aperture in an exterior wall of the tubular body, wherein the aperture is configured to provide a pathway between the lumen and a region external to the tubular body; and a plug mechanically coupled to the tubular body, wherein the plug comprises a protrusion that extends external to the tubular body proximate the aperture, wherein the protrusion is configured to prevent occlusion of the aperture.

In another embodiment there is provided a medical tube comprising: an elongated tube comprising: a tubular body; a lumen that extends along the tubular body to provide a passageway for the removal of fluids and gases; a sealing member on the tubular body that is configured to provide a seal between the tubular body and a body cavity wall; and an aperture in an exterior wall of the tubular body, wherein the aperture is configured to provide a pathway between the lumen and a region external to the tubular body; and a plug coupled to the lumen, wherein the plug comprises a protrusion that extends external to the tubular body proximate the aperture, wherein the protrusion is configured to prevent occlusion of the aperture.

There is also provided a method of manufacturing a medical tube, comprising: providing a medical tube comprising: an elongated tubular body; and a lumen that extends along the tubular body and that is configured to provide a passageway for the removal of fluids and gases, the lumen having an aperture, in an external wall of the tubular body, wherein the aperture is configured to provide a pathway between the lumen and a region external to the tubular body; providing a plug comprising: a body; and a protrusion configured to extend external to the tubular body, wherein the protrusion is configured to prevent occlusion of the aperture; and mechanically coupling the plug to the medical tube.

In yet another embodiment, there is also provided a medical tube comprising: an elongated tubular body; a lumen that extends along the tubular body and that is configured to provide a passageway for the removal of fluids and gases; an aperture in the wall of the tubular body, wherein the aperture is configured to provide a pathway between the lumen and a region external to the tubular body; and an inflatable sealing member comprising: a seal region configured to provide a seal between the elongated tubular body and a body cavity wall when the inflatable sealing member is inflated; and a slot region configured to prevent occlusion of the aperture, wherein the slot region is formed about the exterior of the sealing member, wherein the slot region provides an indentation in the sealing member, wherein the slot region surrounds at least a portion of the aperture, wherein the slot region provides a passage from the region external to the tubular body to the aperture, and wherein the slot region is configured to prevent contact of the aperture to a cavity wall of a patient.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
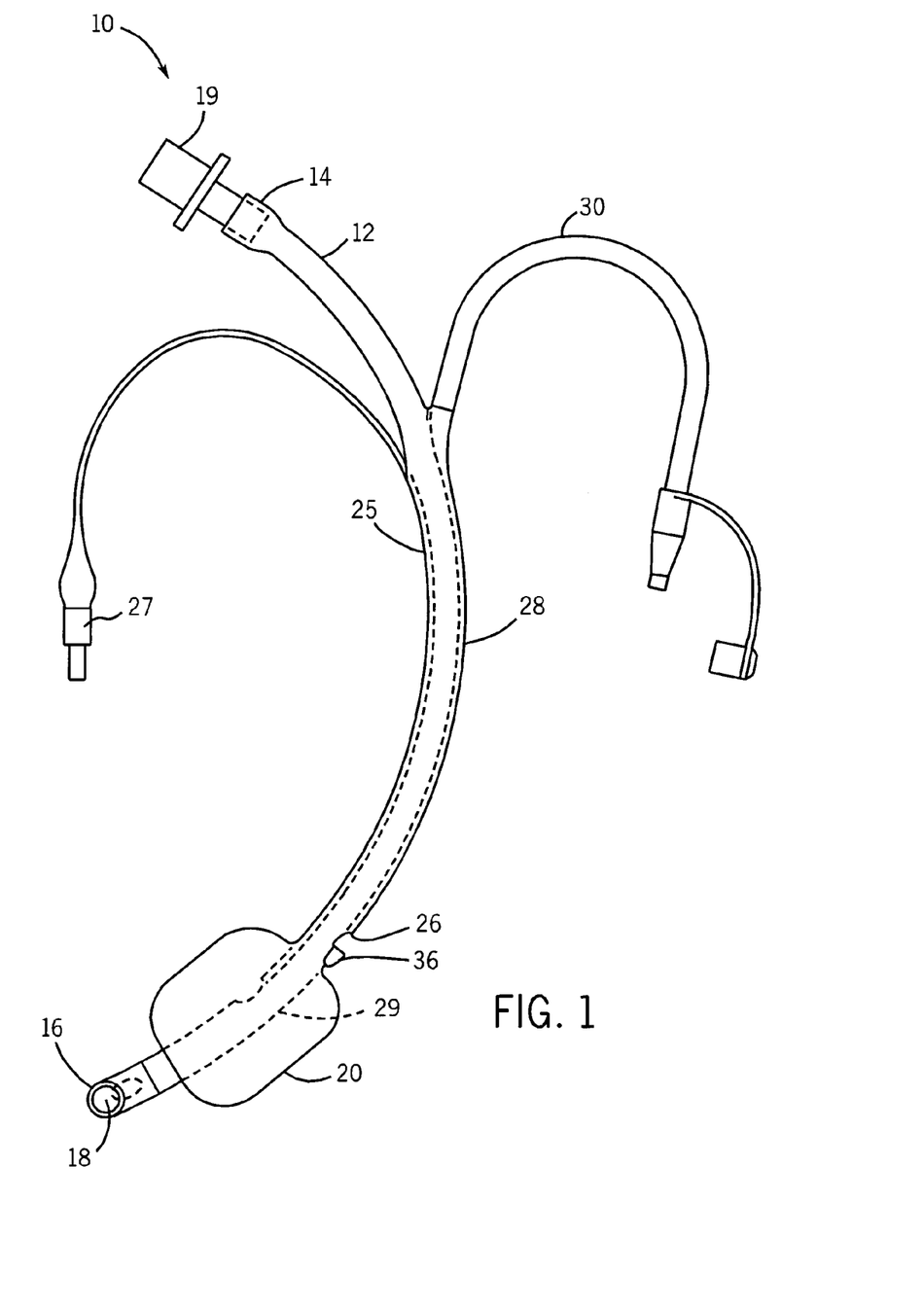
FIG. 1 illustrates an exemplary endotracheal tube with a cuff and plug in accordance with aspects of the present technique.

A variety of medical devices are designed to be inserted with the cavities or passages of the human body. Examples of such medical devices include catheters, stents, feeding tubes, intravenous tubes, breathing tubes, and so forth. The endotracheal tube 10, illustrated in FIG. 1, is an example of such a medical device. As depicted, the endotracheal tube 10 may include a primary tube 12 with a proximal end 14 and distal end 16. The body of the primary tube 12 may define a primary passageway 18 for the transfer of gases or other substances. Further, the proximal end 14 of the primary tube 12 may include a connector 19 that may provide for connection of the endotracheal tube 10 to another medical device, such as a mechanical ventilator used to inject oxygen or other gases into a patient's lungs.

An inflatable cuff 20 may be provided near the distal end 16 of the primary tube 12. During insertion of the endotracheal tube 10 into the trachea of the patient, the cuff 20 may remain uninflated. However, once the endotracheal tube 10 is properly in place, the cuff 20 may be inflated via a syringe (not shown) connected to a proximal end 27 of an inflation lumen 25. Once inflated, the cuff 20 may expand in the trachea 22 of the patient, providing a seal 23 between the endotracheal tube 10 and the tracheal wall 24 (see FIG. 2). The seal 23 created by the cuff 20 in an inflated state may be desirable to prevent gases that are being pumped into the patient from escaping through the trachea 22.

Although the seal 23 between the inflated cuff 20 and the tracheal wall 24 may be beneficial to prevent gases and other substances from escaping through the trachea 22, the seal 23 may also retain secretions of the patient. For example, once the endotracheal tube 10 is inserted into the trachea 22 of the patient and the cuff 20 is inflated, secretions from above the seal 23 may flow down the trachea 22 and settle in a region 21 just above the inflated cuff 20 (see FIG. 2). The build up of secretions may provide a location for pathogens or other infectious substances to form. This potential may be decreased by evacuating the settled secretions and other substances.

Evacuation of the secretions which settle above the cuff 20 may be accomplished by providing a vacuum to suction out the settled secretions. As depicted in FIG. 1, the primary tube 12 of the endotracheal tube 10 may include a fluid removal lumen 28 that extends along the length of the primary tube 12. The fluid removal lumen 28 may terminate at an aperture 26 in the side of the primary tube 12 just above the cuff 20. In one embodiment, a lower fluid removal lumen 29 may continue between the aperture 26 and the distal end 16 of the primary tube 12. If the lower fluid removal lumen 29 is present, it is generally occluded just below the aperture 26 or near the distal end 16 to provide a suction path though the fluid removal lumen 28 and the aperture 26. Accordingly, when the endotracheal tube 10 is inserted into the trachea 22 of the patient with the cuff 20 inflated, the secretions above the cuff 20 may be removed by providing suction in the fluid removal lumen 28. For example, a practitioner may occasionally connect a vacuum to an external fluid removal tube 30 to evacuate the secretions via the fluid removal lumen 28 and the aperture 26.

Although this configuration may generally provide for trouble-free removal of the secretions, difficulty may arise if the aperture 26 becomes occluded. For example, if the aperture 26 nears or contacts the tracheal wall 22, the suction provided by the vacuum through the fluid removal lumen 28 may draw in the tracheal wall 22 to the aperture 26, causing the tissue of the trachea 22 to occlude the aperture 26 and thereby prevent removal of the secretions.

Although the cuff 20 may act to center the primary tube 12 and prevent contact between the tracheal wall 24 and the aperture 26, it has been discovered that in many instances endotracheal tubes 10 do not center about the inflated cuff 20. In light of these realizations, to prevent the tracheal wall 22 from contacting and/or occluding the aperture 26, a bump or protrusion may be provided on the exterior of the primary tube 12 to maintain spacing between the aperture 26 and the tracheal wall 22, thereby preventing occlusion of the aperture 26 during the evacuation process. Manufacturing of such an endotracheal tube 10 may include aligning the bump relative to the aperture, and affixing the bump to the endotracheal tube 10 via an adhesive or other bonding method. This process is often time consuming and labor intensive. Accordingly, it is desirable to provide a raised area, bump or protrusion near the aperture 26 in a manner that does not require bonding of the bump to the endotracheal tube 10 and in a manner that may be easily incorporated into the current manufacturing process.

Figure 2:
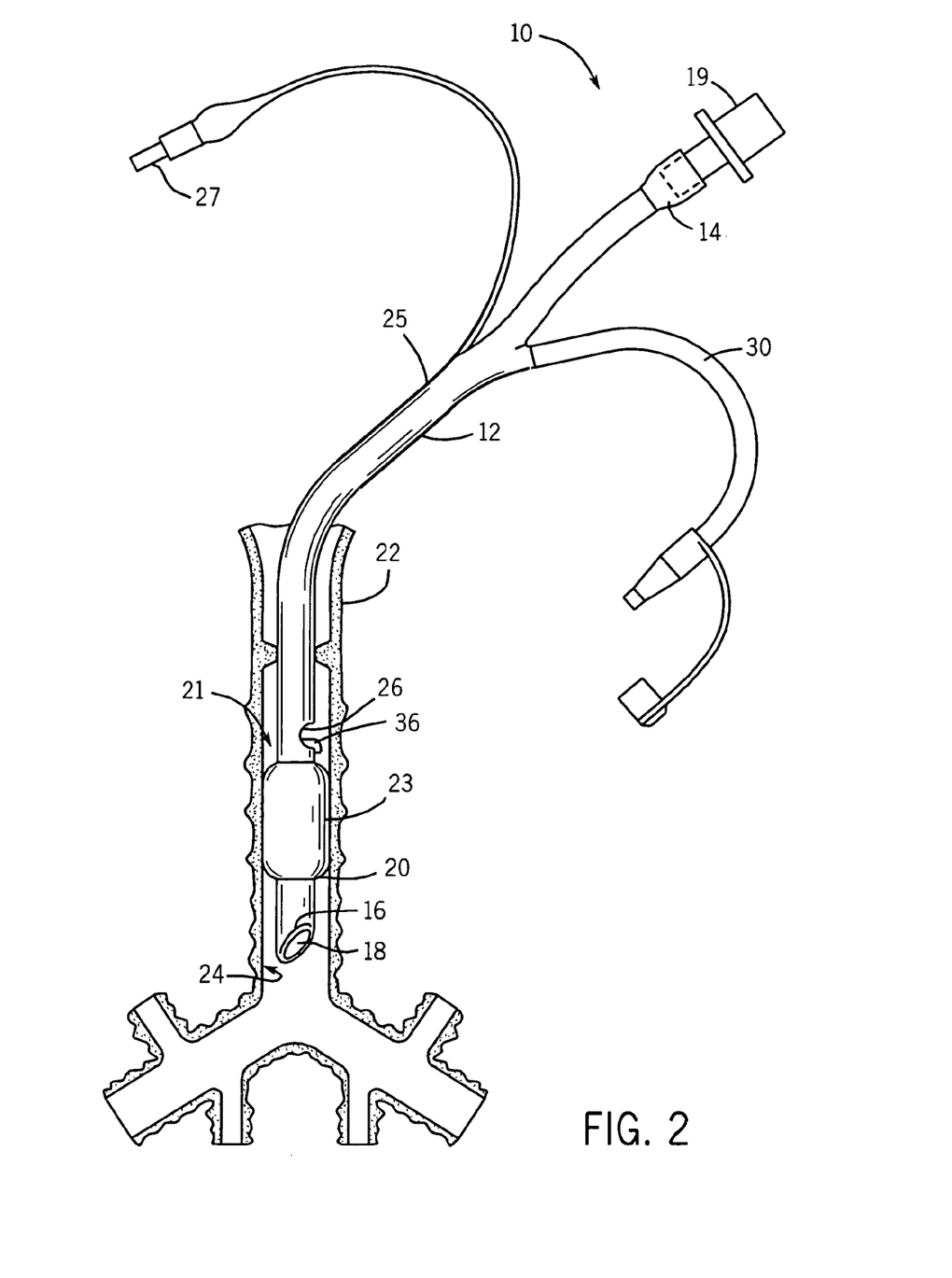
FIG. 2 illustrates the endotracheal tube of FIG. 1 inserted into a patient's trachea in accordance with aspects of the present technique.
Figures 3, 4:
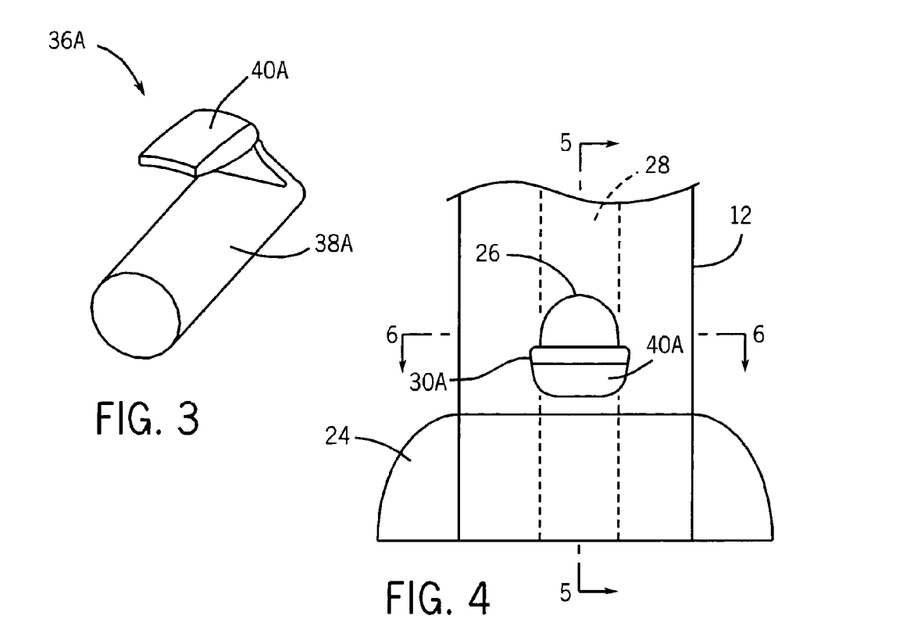
FIG. 3 illustrates a perspective view of an exemplary plug in accordance with aspects of the present technique.
FIG. 4 illustrates a detailed side view of the endotracheal tube of FIG. 1 using the plug of FIG. 3 in accordance with aspects of the present technique.
Figure 5:
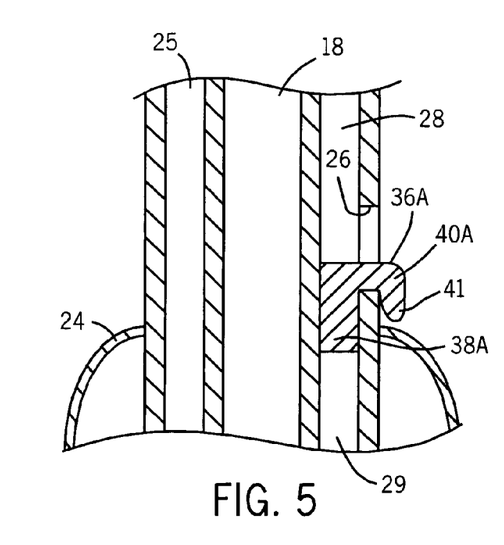
FIG. 5 illustrates a cross sectional view of the endotracheal tube of FIG. 4 taken along line 5-5 of FIG. 4.
Figure 6:
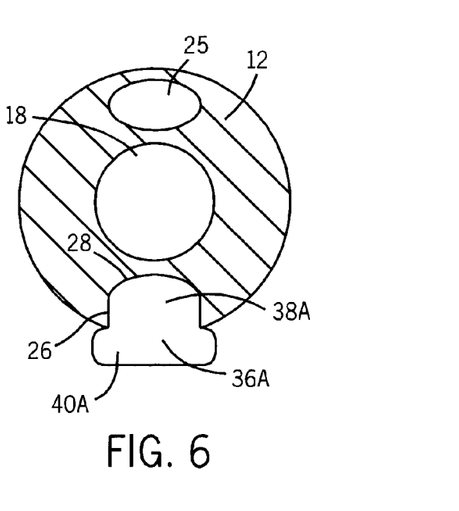
FIG. 6 illustrates a cross sectional view of the endotracheal tube of FIG. 4 taken along 6-6 of FIG. 4.
Figures 7, 8:
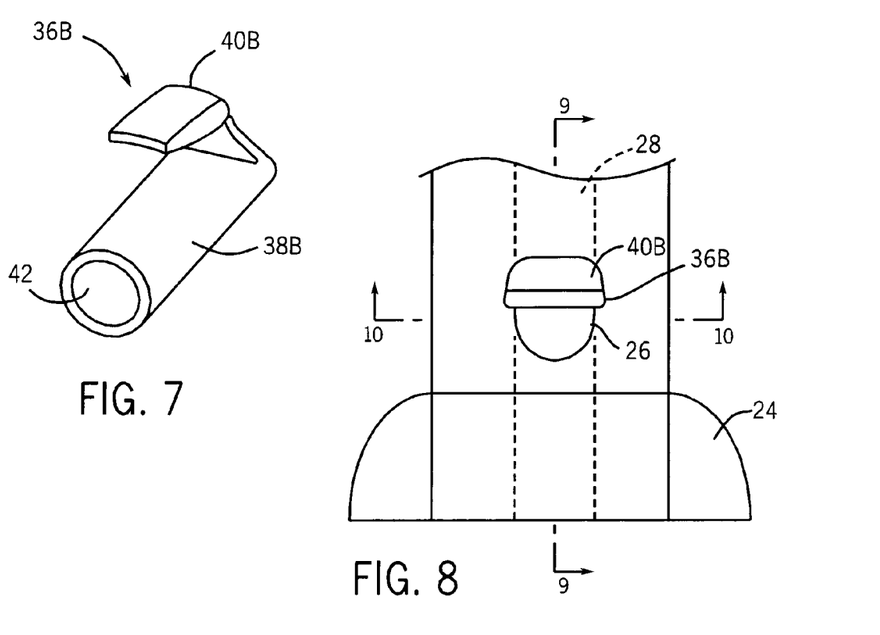
FIG. 7 illustrates a perspective view of an alternate plug configuration in accordance with aspects of the present technique.
FIG. 8 illustrates a detailed side view of the endotracheal tube of FIG. 1 using the plug of FIG. 7 in accordance with aspects of the present technique.

As shown in FIGS. 1 and 2, this issue may be addressed by utilizing a plug 36 that may mechanically and/or adhesively couple to the endotracheal tube 10 to provide a protrusion near the aperture 26. Turning now to FIG. 3, in one embodiment, a plug 36A may include a body 38A and a protrusion 40A. The body 38A may provide for mechanically coupling the plug 36A to the endotracheal tube 10, and the protrusion 40A may provide for separation of the aperture 26 from the tracheal wall 22. For example, as depicted in FIG. 3, the body 38A of the plug 36A may be shaped to provide for mating of the body 38A into the lower fluid removal lumen 29 of the endotracheal tube 10. As depicted in FIGS. 5, 6 and 7, the body 38A may be inserted into the lower fluid removal lumen 29 such that the body 38A occludes the lower fluid removal lumen 29.

In one embodiment, the plug 36A may be secured to the lower fluid removal lumen 29 via an interference fit between the body 38A and the walls of the lower fluid removal lumen 29. For example, as depicted in FIGS. 3, 4, 5 and 6, the body 38A of the plug 36A may take on the general shape of the respective lumen where it is inserted (i.e., the shape of the fluid removal lumen 28 or the lower fluid removal lumen 29). As depicted, the body 38A has a similar oval shape as the oval shape of the fluid removal lumen 28 and the lower fluid removal lumen 29. In another embodiment, the plug 36A may be secured to the lower fluid removal lumen 29 by applying an adhesive or solvent bonding agent between the plug 36A and the wall of the lower fluid removal lumen 29. As will be appreciated by a person of ordinary skill in the art, the plug 36A may be secured to the endotracheal tube 10 by any means which properly seats the plug 36A relative to the aperture 26. For example, the gap between the body 38A and the protrusion 40 may be small enough such that the plug 36A may be clipped about the external surface of the primary tube 12 and the wall of the lower fluid removal lumen 29. In such a configuration, the plug 36A is secured by an interference fit that may be aided by the application of an adhesive or a solvent. Other methods to secure the plug 36A to the endotracheal tube 10 may include ultrasonic welding or thermal bonding.

In addition to securing the plug 36A, inserting the body 38A of the plug 36A into the lower fluid removal lumen 29 may provide for occluding the lower fluid removal lumen 29. For example, in one embodiment, the fluid removal lumen 28 and the lower fluid removal lumen 29 may extend the entire length of the primary tube 12. Therefore, if the lower fluid removal lumen 29 is not occluded, a vacuum provided through the fluid removal lumen 28, via external fluid removal tube 30, may result in suction through both the aperture 26 and the distal end of the lower fluid removal lumen 29. By configuring the plug 36A such that it occludes the lower fluid removal lumen 29, the suction provided by the vacuum may be limited to the opening of the aperture 26. As will be appreciated by a person of ordinary skill in the art, the plug 36A will occlude the lower fluid removal lumen 29 because it completely fills the cavity of the lower fluid removal lumen 29.

To provide for separation of the aperture 26 from the tracheal wall 22, the plug 36A may include a protrusion 40 that extends outwardly from the exterior of the primary tube 12. In the embodiment depicted in FIGS. 3-6, when the body 38A of the plug 36A is inserted into the lower fluid removal lumen 29, the protrusion 40A extends external to the primary tube 12 at or near the aperture 26. The protrusion 40A may vary in size and shape to provide a sufficient separation between the aperture 26 and the tracheal wall 24, while maintaining a low enough profile to allow the tracheal tube 10 to be comfortably inserted into the trachea 22 of the patient. For example, the protrusion 40A may include only a raised area extending out of the aperture 26, and may not include the clip 41 which extends external to the tube in a direction parallel to a longitudinal axis of the primary tube 12.

Figure 9:
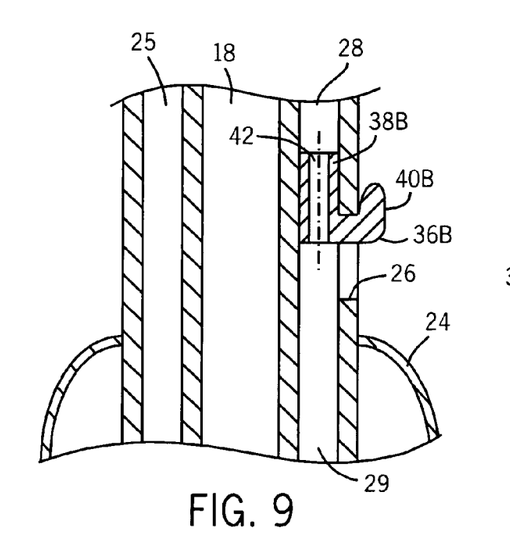
FIG. 9 illustrates a cross sectional view of the endotracheal tube of FIG. 8 taken along line 9-9 of FIG. 8.
Figure 10:
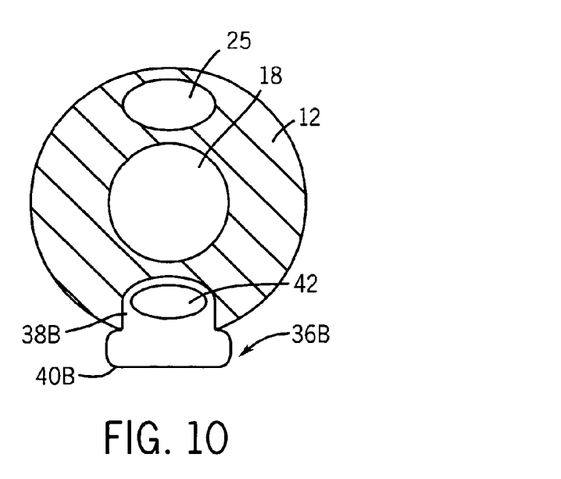
FIG. 10 illustrates a cross sectional view of the endotracheal tube of FIG. 8 taken along line 10-10 of FIG. 8.

In another embodiment, a plug 36B may also be secured to the fluid removal lumen 28 instead of the lower fluid removal lumen 29 as discussed above. For example, as depicted in FIGS. 7, 8, 9 and 10, the plug 36B, may be inserted into the fluid removal lumen 28 wherein the protrusion 40B is located on the edge of the aperture 26 opposite the cuff 20, i.e., the upper edge of the aperture 26. In such a configuration, the plug 36B may also include a passage 42 to provide a pathway for secretions near the aperture 26 to be drawn through the fluid removal lumen 28. For example, when a vacuum is applied to the fluid removal lumen 28 via the external fluid removal tube 30, secretions may travel through the aperture 26 and through the passage 42 of the plug 36B as shown in FIG. 9. As depicted, the passage 42 may take the form of a hole extending the length of the body 38B. As will be appreciated by a person of ordinary skill in the art, the size, shape and orientation of the passage 42 may be varied to accommodate various applications. For example, the size of the passage 42 may be increased in an embodiment where the body 38B is not used to provide radial support to the surrounding walls of the fluid removal lumen 28. In another embodiment, the body 38B of the plug 36B may not substantially fill the cross-section of the fluid removal lumen 28. For example, the body 38B may include a semi-circular region that provides for occluding only half of the cross-section of the fluid removal lumen 28. In such an embodiment, the plug 36B may be secured to the top of the aperture 26 with an interference fit between the body 38B and the protrusion 40B, as well as by adhesives.

Figure 11:
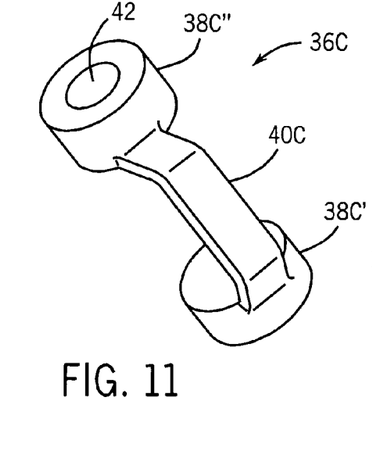
FIG. 11 illustrates a perspective view of another alternate plug configuration in accordance with aspects of the present technique.
Figure 12:
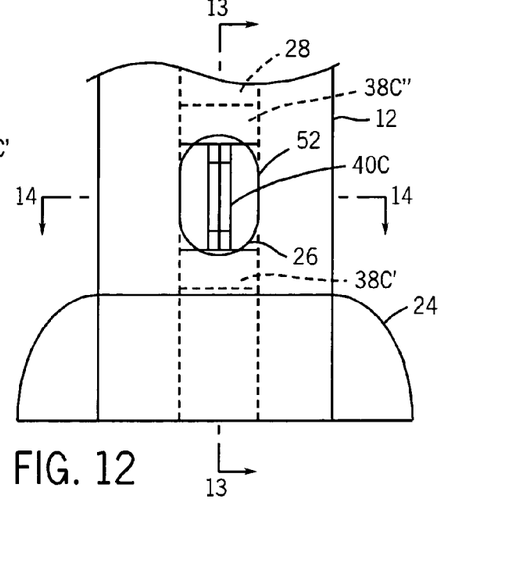
FIG. 12 illustrates a detailed side view of the endotracheal tube of FIG. 1 using the plug of FIG. 11 in accordance with aspects of the present technique.
Figure 13:
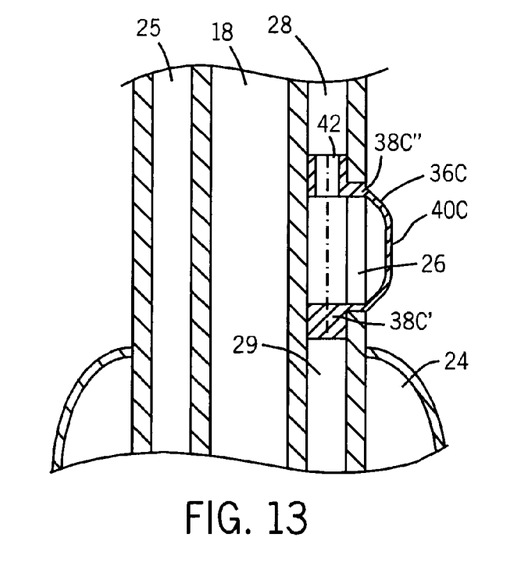
FIG. 13 illustrates a cross sectional view of the endotracheal tube of FIG. 12 taken along line 13-13 of FIG. 12.
Figure 14:
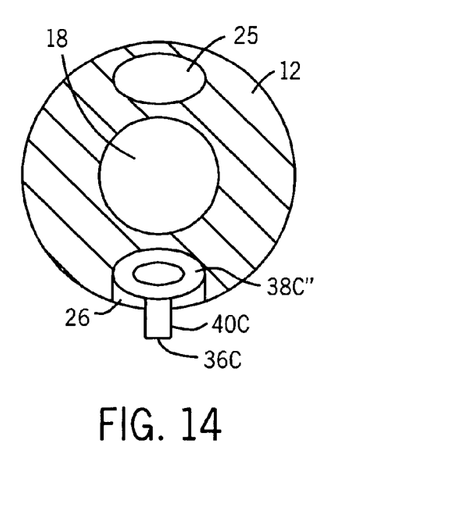
FIG. 14 illustrates a cross sectional view of the endotracheal tube of FIG. 12 taken along line 14-14 of FIG. 12.

Turning now to FIG. 11, another embodiment of a plug 36C is depicted. To prevent occlusion and to integrate with manufacturing, the protrusion 40C may include an arch that extends across the aperture 26. For example, as depicted in FIG. 11, the body 38C of the plug 36C may include a first body portion 38C', a second body portion 38C" to support the arch shaped protrusion 40C. The first body portion 38C' of the plug 36C may be inserted into the lower fluid removal lumen 29, and the second body portion 38C" of the plug 36C may be inserted into the fluid removal lumen 28, as depicted in FIGS. 12 and 13. As will be appreciated by a person of ordinary skill in the art, the body 38C may be modified to accommodate various requirements and may include the features of the body 38A or 38B described above. For example, the diameters and shapes of the first body portion 38C' and/or the second body portion 38C" may be modified to provide an interference fit, fluid flow, or occlusion of the lower fluid removal lumen 29.

In one embodiment, the arch-shaped protrusion 40C may span the region between the first body portion 38C' and the second body portion 38C" as depicted in FIG. 11. The plug 36C may include a single arch-shaped protrusion 40C with a semi-circular shape to provide for patient comfort during insertion and removal of the endotracheal tube 10. When the lower body and upper body protrusions of the plug 36C are properly seated, the arch-shaped protrusion 40C may extend external to the primary tube 12. The arch-shaped protrusion 40C may provide for spacing between the aperture 26 and the tracheal wall 24 and thereby prevent occlusion across the aperture 26. As will be appreciated by a person of ordinary skill in the art, the configuration of the plug 36C and arch-shaped protrusion 40C may be modified to accommodate various requirements. For example, the plug 36C may include multiple arch-shaped protrusions 40C.

To accommodate the insertion of the first body portion 38C' of the plug 36C depicted in FIG. 11, the aperture 26 may take different forms. For example, as depicted in FIG. 12, the aperture 26 may take an oblong slot as opposed to a generally circular shape. In an embodiment, the aperture 26 may allow for the first body portion 38C' and the second body portion 38C" to be inserted into the slot 52 portion of aperture 26 and subsequently slide them into their respective locations in the lower fluid removal lumen 29 and fluid removal lumen 28 (see FIG. 13). For example, assembling the plug 36C to the endotracheal tube 10 may include depressing the first body portion 38C' and the second body portion 38C" to resist the biasing force of the arch-shaped protrusion 40C. Then the first body portion 38C' and the second body portion 38C" may be placed into the fluid removal lumen 28, via the aperture 26. Once in the fluid removal lumen 28, the first body portion 38C' and the second body portion 38C" may be released, allowing the biasing force of the arch-shaped protrusion 40C to seat the first body portion 38C' in the lower fluid removal lumen 29 and the second body portion 38C" in the fluid removal lumen 28. As will be appreciated by a person of ordinary skill in the art, the configuration of the aperture may be modified to accommodate the insertion of the plug 36C and the desired fluid flow. For example, the aperture may include a segment of wider diameter to for insertion of the first and second body portions 38C' and 38C", while maintaining a slot shaped top and bottom to allow the arch-shaped protrusion 40C to expand in either direction, while substantially enclosing the first and second body 38C' and 38C" in the lumens 28 and 29.

Figure 15:
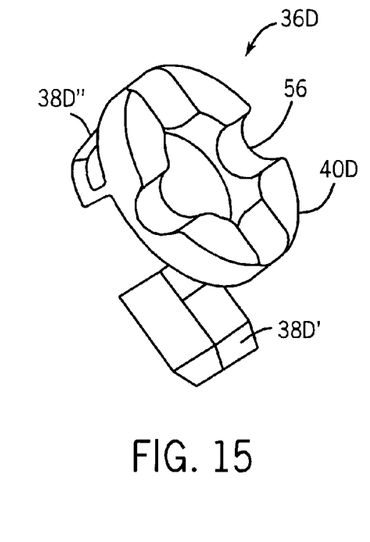
FIG. 15 illustrates a perspective view of yet another alternate plug configuration in accordance with aspects of the present technique.
Figure 16:
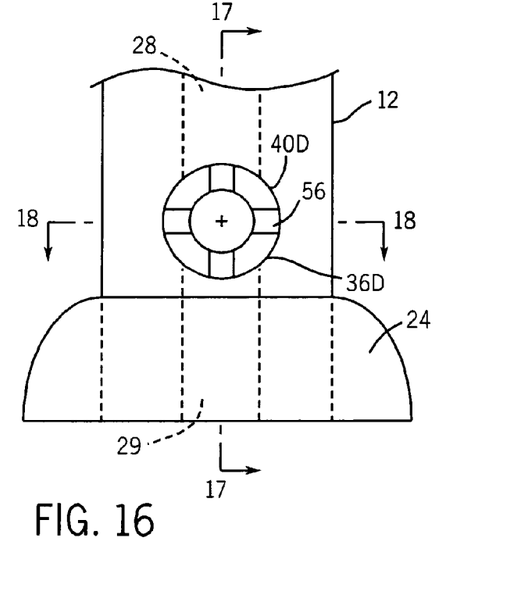
FIG. 16 illustrates a detailed side view of the endotracheal tube of FIG. 1 using the plug of FIG. 15 in accordance with aspects of the present technique.
Figure 17:
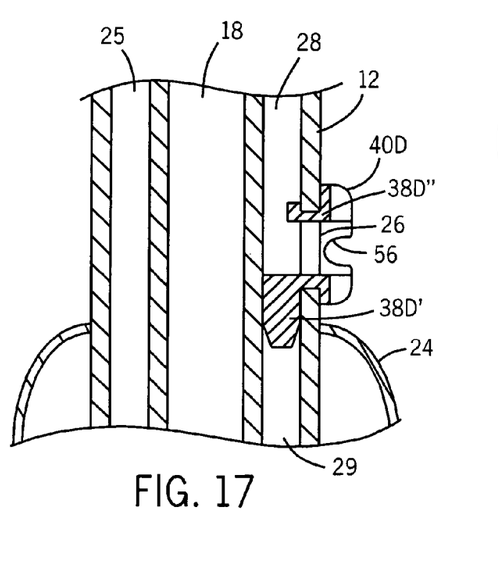
FIG. 17 illustrates a cross sectional view of the endotracheal tube of FIG. 16 taken along line 17-17 of FIG. 16.

In addition to the previous embodiment, another embodiment may provide for a protrusion that surrounds a majority of aperture 26. Turning now to FIG. 15, the plug 36D may prevent occlusion of the aperture 26 with an annular protrusion 40D that extends about the periphery of the aperture 26. For example, as depicted in FIG. 17, an embodiment of the plug 36D may include an annular protrusion 40D that is raised from the surface of the primary tube 12, while also including channels 56 that allow for the passage of fluids. As will be appreciated by a person of ordinary skill in the art, the design of the annular protrusion 40D may be varied. For example, the number, size and shape of the channels 56 may be modified for various applications (e.g., the number of channels may be increased to eight, or the channels may include though holes in the side of the ring 54). Additionally, the design of the annular protrusion 40D may include features to increase patient comfort (e.g., a lower profile or smoothed edges).

Figure 18:
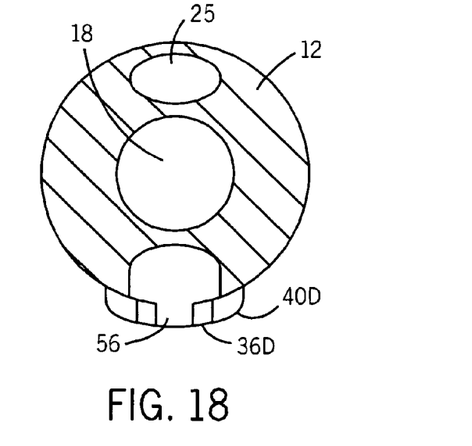
FIG. 18 illustrates a cross sectional view of the endotracheal tube of FIG. 16 taken along line 18-18 of FIG. 16.

Further, in one embodiment, the annular protrusion 40D may be secured to the primary tube 12 via a body 38D that includes first body portion 38D' and a second body portion 38D". For example, the first body portion 38D' may be inserted into the lower fluid removal lumen 29 (see FIGS. 17 and 18) and secured via an interference fit and adhesives, in a manner similar to the embodiments described above. The second body portion 38D" may provide for attachment of the plug 36D to the primary tube 12 via insertion of the second body portion 38D" into the lower fluid removal lumen 29 in a manner similar to the embodiments described previously. For example, FIG. 17 depicts the second body portion 38D" as a lip that may be extended into the fluid removal lumen 28 and secure itself to the wall of the fluid removal lumen 28. As will be appreciated by a person of ordinary skill in the art, securing the plug 36D with the annular protrusion 40D may be varied to accommodate various applications. For example, the plug 36D may be secured to the lumens 28 and 29 by either one of or both of the first body portion 38D' and/or the second body portion 38D". Further, the first body portion 38D' and the second body portion 38D" may be modified to accommodate features discussed previously (e.g., a hole in the second body portion 38D" to allow fluid flow).

To accommodate the required mechanical design constraints, as well as the comfort of the patient, various materials may be used to form the various embodiments of the plug 36. In one embodiment, a thermoplastic may be used to form the plug 36. For example, the plug 36 may be formed from polyvinyl chloride (which may be plasticized and/or filled with radioopaque material), polypropylene, polyethylene, polyurethane, thermoplastic elastomers, rubbers, silicones, ABS, or nylon. One embodiment may include a material with a durometer of less than Shore A 90, typically less than 80. In another embodiment, multiple materials may be used to form the plug 36. For example, the a rigid material may be used to form the body 38 while a material with a lower durometer rating may be used to form the protrusion 40 in order to increase patient comfort. To form the plug 36, any suitable forming techniques may be used, such as injection molding and casting. In addition, the materials used for the plug may include additives incorporated into the mixture to provide additional features, such as radioopacity, anti-microbial properties, low friction, or other desired properties.

Indeed, any suitable manufacturing process may be used to manufacture a medical device that includes a plug 36. For example an endotracheal tube 10 that includes a fluid removal lumen 28 extending longitudinally along the exterior wall of the primary tube 12 may be manufactured or otherwise provided or obtained. As will be appreciated by a person of ordinary skill in the art, providing a tube with a lumen 28 may not be limited to endotracheal tubes 10, but may include other tubes or medical devices which include a pathway for the evacuation of secretions, fluids, or gasses. For example, a tube with a fluid removal lumen may include catheters, stents, feeding tubes, intravenous tubes, breathing tubes, as described previously. The fluid removal lumen 28 includes an aperture 36 that provides a contiguous pathway from the fluid removal lumen 28 (or other evacuation path) into the region 21 where secretions may collect. For example, the aperture 26 may be provided by cutting or otherwise forming a hole in the exterior of the primary tube 12, wherein the hole is configured to terminate into the fluid removal lumen 28. A plug 36 is also manufactured or otherwise provided or obtained. The plug 36 may then be coupled to a lumen of the tube 10. For example, coupling the plug 36 to a lumen 28 and/or 29 may include inserting the body 38 of the plug 36 to the appropriate fluid removal lumen(s) 28 and/or 29 to provide mechanical, solvent and/or adhesive coupling.

Figure 19:
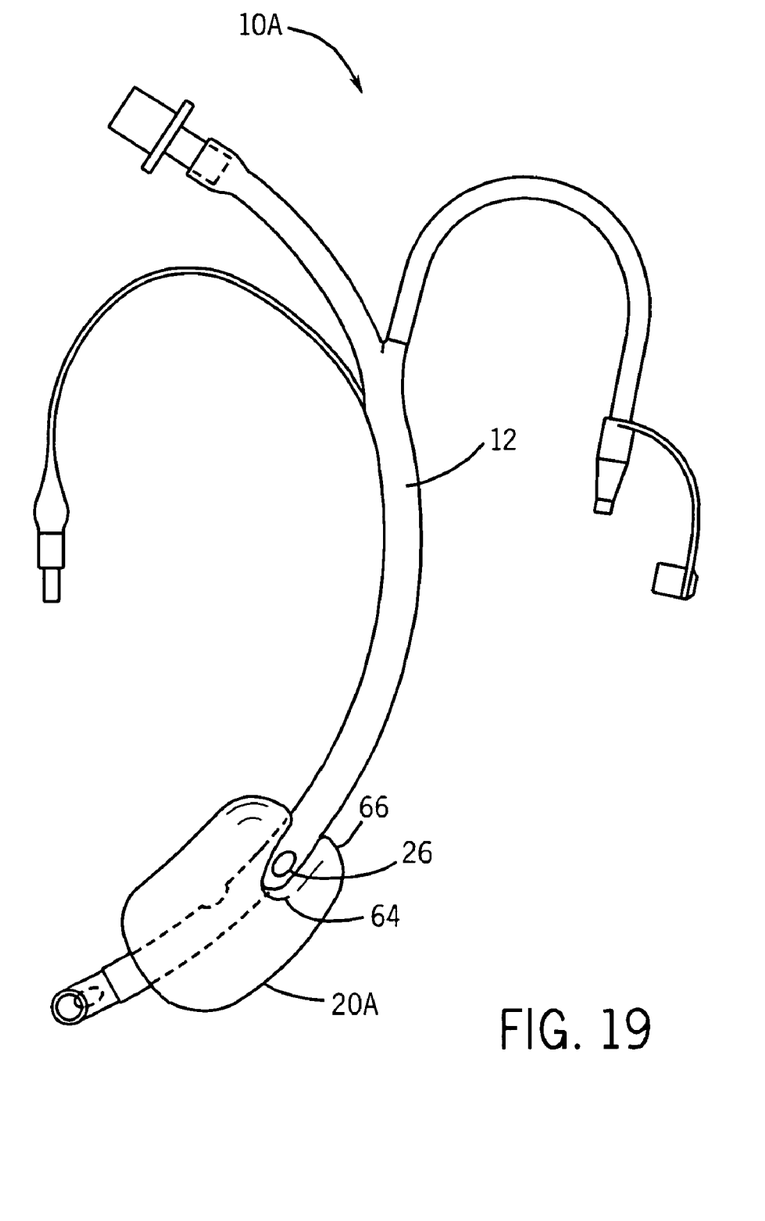
FIG. 19 illustrates an endotracheal tube with a slotted inflatable cuff in accordance with aspects of the present technique.

In another embodiment, it may also be desirable that the inflatable cuff 20 be configured to prevent occlusion of the aperture 26. For example, as depicted in FIG. 19, the cuff 20A may be formed to include a cuff slot 64 to provide a protrusion surrounding the aperture 26. In one embodiment, the cuff 20A may be secured about the primary tube 12, such that the slot opening 66 is oriented to provide for secretions of the trachea 22 above the cuff 20A to collect in the slot 64 and access the aperture 26. The cuff 20A may also maintain a separation between the tracheal wall 24 and the aperture 26. As will be appreciated by a person of ordinary skill in the art, the size shape and configuration of the cuff 20A may be varied to accommodate various applications (e.g., the slot 64 in the cuff may be varied in width, length, and shape). For example, the slot may include an "L" shape to provide added support about the aperture 26.

The cuff 20A and slot 64 may provide for the collection of secretions. As depicted in FIG. 20, the cuff 20A may inflate and expand to create a seal against the tracheal wall 22 (see FIG. 2) allowing the slot 64 to collect secretions and funnel them toward the aperture 26. As will be appreciated by a person of ordinary skill in the art, the slot 64 and the opening 66 may be modified to accommodate various requirements. For example, the slot opening 66 may be substantially wider in size with the slot 64 narrowing about the aperture 26.

While the invention may be susceptible to various modifications and alternative forms, specific embodiments have been shown by way of example in the drawings and have been described in detail herein. However, it should be understood that the invention is not intended to be limited to the particular forms disclosed.

Rather, the invention is to cover all modifications, equivalents, and alternatives falling within the spirit and scope of the invention as defined by the following appended claims.

What is claimed is:

1. A medical tube lumen plug, comprising:
a body configured to be mechanically coupled to a lumen of a medical tube proximate an aperture in the tube, wherein a portion of the body is coupled within the lumen; and
a protrusion configured to extend external to the medical tube to hold the aperture away from a body cavity wall to prevent occlusion of the aperture, wherein the aperture is configured to provide a pathway between the lumen and a region external to the medical tube, and wherein the body covers only a portion of the aperture.

2. The plug of claim 1, wherein the body is configured to be disposed only in an upper portion of the aperture.

3. The plug of claim 1, wherein the protrusion comprises a bump.

4. The plug of claim 1, wherein the protrusion comprises an arch configured to span the aperture.

5. The plug of claim 1, wherein the protrusion comprises a ring, wherein the ring is configured to at least partially surround a periphery of the aperture, and wherein the ring comprises an opening configured to provide a pathway between the aperture and the region external to the medical tube.

6. The plug of claim 1, wherein the body is coupled within the lumen using solvent bonding or adhesive bonding.

7. The plug of claim 1, wherein the body comprises a first body portion a second body portion.

8. The plug of claim 7, wherein the second body portion comprises a hole, wherein the hole is configured to provide a passageway through the second body portion.

9. The plug of claim 1, wherein the body comprises polyvinyl chloride, polypropylene, polyethylene, polyurethane, thermoplastic elastomers, rubbers, silicones, acrylonitrile butadiene styrene, or nylon.

10. A medical tube comprising:
an elongated gas-conveying tube
a lumen that extends along gas-conveying tube to provide a passageway for the removal of fluids and gases;
a sealing member on the tubular body that is configured to provide a seal between the tubular body and a body cavity wall; and
an aperture in an exterior wall of the tubular body adjacent the sealing member, wherein the aperture is configured to provide a pathway between the lumen and a region external to the tubular body; and
a plug coupled to the tubular body in the aperture, wherein the plug comprises a protrusion that extends external to the tubular body and wherein the plug is coupled proximate the aperture, wherein the protrusion is configured to hold the aperture away from the body cavity wall to prevent occlusion of the aperture by the body cavity wall, and wherein the plug is positioned relative to the aperture such that a flow path through the aperture in a direction generally perpendicular to a path of the suction lumen is unobstructed.

11. The medical tube of claim 10, wherein the protrusion comprises a bump.

12. The medical tube of claim 10, wherein the protrusion comprises an arch configured to span the aperture.

13. The medical tube of claim 10, wherein the protrusion comprises a ring, wherein the ring is configured to at least partially surround a periphery of the aperture, and wherein the ring comprises a channel configured to provide a pathway between the aperture and the region external to the medical tube.

14. The medical tube of claim 10, wherein the plug is mechanically coupled within the lumen.

15. The medical tube of claim 10, wherein mechanical coupling is facilitated by the use solvent bonding or adhesive bonding between the plug and the elongated tube.

16. The medical tube of claim 10, wherein the plug comprises polyvinyl chloride, polypropylene, polyethylene, polyurethane, thermoplastic elastomers, rubbers, silicones, acrylonitrile butadiene styrene, or nylon.

17. The medical tube of claim 10, wherein the aperture comprises a circular or elliptical hole.

18. The medical tube of claim 10, wherein the aperture comprises a slot.

19. A medical tube comprising:
a tubular body;
a lumen that extends along the tubular body to provide a passageway for the removal of fluids and gases;
a sealing member on the tubular body that is configured to provide a seal between the tubular body and a body cavity wall; and
an aperture in an exterior wall of the tubular body, wherein the aperture is configured to provide a pathway between the lumen and a region external to the tubular body, wherein the pathway is generally orthogonal to the lumen; and
a plug coupled to the lumen proximate the aperture, wherein a portion of the plug is coupled within the lumen, wherein the plug comprises a protrusion that extends external to the tubular body proximate the aperture, wherein the protrusion is configured to prevent occlusion of the aperture.

20. The medical tube of claim 19, wherein the plug coupled to the lumen, comprises a mechanical coupling between the plug and the lumen.

21. The medical tube of claim 19, wherein the plug coupled to the lumen comprises an adhesive between the plug and the lumen.

22. The medical tube of claim 19, wherein the plug is configured to provide occlusion of at least a portion of the lumen.

23. The medical tube of claim 19, wherein the protrusion comprises a bump.

24. The medical tube of claim 19, wherein the protrusion comprises an arch configured to span the aperture.

25. The medical tube of claim 19, wherein the protrusion comprises a ring, wherein the ring is configured to at least partially surround a periphery of the aperture, and wherein the ring comprises a channel configured to provide a pathway between the aperture and the region external to the medical tube.

26. The medical tube of claim 19, wherein the plug comprises a first body portion and a second body portion, and wherein the first body portion and the second body portion are configured to be coupled to the lumen.

27. The medical tube of claim 26, wherein the second body portion comprises a hole, wherein the hole is configured to provide a passageway through the second body.

28. The medical tube of claim 19, wherein the plug is formed from polyvinyl chloride, polypropylene, polyethylene, polyurethane, thermoplastic elastomers, rubbers, silicones, acrylonitrile butadiene styrene, or nylon.

29. The medical tube of claim 19, wherein the aperture comprises a circular or elliptical hole.

30. The medical tube of claim 19, wherein the aperture comprises a slot.

31. A method of manufacturing a medical tube, comprising: providing:
- an elongated gas conveying tubular body;
- a sealing cuff mounted on the body, wherein the sealing cuff is configured to seal against the wall of a body cavity; and
- a lumen that extends along the tubular body and that is configured to provide a passageway for the removal of fluids and gases, the lumen having an aperture, in an external wall of the tubular body, wherein the aperture is configured to provide a pathway between the lumen and a region external to the tubular body;

providing a plug comprising:
- a protrusion configured to extend external to the tubular body, wherein the protrusion is configured to prevent occlusion of the aperture, and wherein the protrusion covers only a portion of the aperture; and
- mechanically coupling the plug to the medical tube proximate the aperture, wherein a portion of the body is coupled within the lumen.

32. The method of manufacturing a medical tube of claim 31, comprising cutting the aperture.

33. The method of manufacturing a medical tube of claim 31, wherein mechanically coupling the plug to the medical tube comprises inserting the body of the plug into the lumen.

34. The method of manufacturing a medical tube of claim 31, wherein mechanically coupling the plug to the medical tube comprises securing the body to the lumen using solvent bonding or adhesive bonding.

35. The method of manufacturing a medical tube of claim 31, wherein providing a plug comprises forming the plug from polyvinyl chloride, polypropylene, polyethylene, silicones, acrylonitrile butadiene styrene, or nylon.

* * * * *